United States Patent [19]

Szirtes

[11] Patent Number: 4,630,203
[45] Date of Patent: Dec. 16, 1986

[54] CONTOUR RADIOGRAPHY: A SYSTEM FOR DETERMINING 3-DIMENSIONAL CONTOURS OF AN OBJECT FROM ITS 2-DIMENSIONAL IMAGES

[76] Inventor: Thomas Szirtes, 9 Fourwinds Drive, Unit 910, Downsview, Ontario, M3J 2S8, Canada

[21] Appl. No.: 565,932

[22] Filed: Dec. 27, 1983

[51] Int. Cl.$^4$ ....................... G01B 11/24; G06F 15/42
[52] U.S. Cl. .......................................... 364/414; 356/2
[58] Field of Search ................ 364/414; 356/2; 353/5, 353/6, 7; 350/130, 136; 378/41

[56] References Cited

U.S. PATENT DOCUMENTS 4,099,880 7/1978 Kano .................................... 356/2 X Primary Examiner—Jerry Smith
Assistant Examiner—Clark A. Jablon
Attorney, Agent, or Firm—McCarthy & McCarthy

[57] ABSTRACT

A method and apparatus for reconstructing the three-dimensional coordinates of an identifiable contour on an object without relying on markers or pre-existing knowledge of the geometry of the object is described. The technique is defined as Contour Radiography. In the preferred embodiment two X-ray sources irradiate an object possessing a radiographically identifiable contour and then the two images of the contour are projected onto an X-ray film at spaced locations on the film plane. These images are digitized by the tracing of the image curves with a cursor or some other means thereby establishing the coordinates of an arbitrary number of image points. The digital data thus obtained is processed in accordance with a Contour Radiography (CONRAD) algorithm to identify corresponding points on the two curves which originate from the same point on the physical contour. The spatial coordinates of the X-ray sources are determined using a special calibration system. Then the coordinates of each corresponding point pair are processed with the spatial coordinates of the X-ray source to determine the three-dimensional coordinates of their originating space-point on the contour. In this way the three-dimensional coordinates of the contour are determined. The three-dimensional coordinates are then processed in a commercially available graphics system to visually display the reconstructed contour. The technique has particular application in medicine for determining the undistorted shape, position, size and orientation of selected internal organs, such as bone, which have a radiographically identifiable contour.

16 Claims, 15 Drawing Figures i = sequential number of a point on curve $C_A$ j = sequential number of a point on curve $C_B$

CONTOUR RADIOGRAPHY: A SYSTEM FOR DETERMINING 3-DIMENSIONAL CONTOURS OF AN OBJECT FROM ITS 2-DIMENSIONAL IMAGES

The present invention relates to a system for determining three-dimensional contours of an object from its two-dimensional images. In particular, the invention relates to a system for determining the shape, size, position and configuration of internal human organs which possess radiographically-recognizable contours.

One known system which has found relatively wide application, which is based on the principles of stereophotogrammetry, is described in Van Der Plaats, G. J., "Medical X-Ray Techniques", 1960, Cleaverhume, London; McNeil, G. T., "X-Ray Stereo Photogrammetry", "Photogrammetric Engineering", Vol. 32, 1966, pp. 993–1004 and Hallert, B., "X-Ray Photogrammetry", 1970, Elsevier, Amsterdam. In this technique a stereo pair of radiographs is obtained by exposing the patient to two non-coincident X-ray sources while the x-ray film plane is kept identical. The three-dimensional geometry of the target organ is then reconstructed from its two two-dimensional images by employing standard optical or analytical photogrammetric procedures.

A related system for the in vivo measurement of the spatial location and orientation of internal organs is bi-plane radiography. In this method, unlike in stereophotogrammetry, the two X-ray film planes are different. A possible computer-aided method for the measurement of the three-dimensional geometry of the cervical spine was proposed by Suh, C. H. ("The Fundamentals of Computer Aided X-Ray Analysis of the Spine", Journal of Biomechanics, Vol. 7, 1974, pp. 161–169) who developed an analytical technique in which the film planes were considered orthogonal. Similar systems were proposed by Schock, C. C., et al "An In Vivo Method for Three Dimensional Analysis of the Displacement of Spinal Segements", Journal of Bone and Joint Surgery, News Notes, Vol. 55-A, 1973, pp. 435; Brown, R. H., "Instrumental System for Two Plane Radiographic Analysis", Masters Thesis, School of Engineering, Case Western Reserve University, 1972; Brown, R. H., et al "Spinal Analysis Using a Three-Dimensional Radiographic Technique", Journal of Biomechanics, Vol. 9, 1976, pp. 355–365 but with a more refined analysis which was used for the measurement of the thoracolumbar spinal orientation of scoliotic patients.

The basic principle of descriptive geometry used both in the aforecited analytical stereophotogrammetry and bi-plane radiography is identical. It involves the determination of the three coordinates of a point in space from the two coordinates of each of its two images, the positions of the two X-ray sources and of the X-ray film planes. Once the spatial coordinates of at least three points on an anatomical rigid body are determined as above, the spatial location and orientation of the body itself can be calculated.

In all of the above systems the major problem lies in the definition of the points on the object body and, even more importantly, in the identification of their images in the radiographs. In order to try to overcome this problem, radio-opaque objects (serving as artificial 'landmarks' such as small metallic spheres have deliberately been inserted in patients. This method is described in Selvik, G., "A Roentgen Stereophotogrammetry Method for the Study of the Skeletal System", Thesis, Department of Anatomy, University of Lund, Lund, Sweden, 1974; Olsson, T. H. et al. "Mobility of the Lumbosacral Spine After Fusion Studies and the Aid of Roentgen Stereophotogrammetry", Clinical Orthopaedics and Related Research, No. 129, 1977, pp. 181–190; Veress, S. A. et al. "Patellar Tracking Patterns Measurement by Analytical X-Ray Photogrammetry", Journal of Biomechanics, Vol. 12, 1979, pp. 639–650.

The use of natural anatomic landmarks has also been reported; Suh, C. H. "The Fundamentals of Computer Aided X-Ray Analysis of the Spine", Journal of Biomechanics, Vol. 7, 1974, pp. 161–169; Schock, C.C. et al. "An In Vivo Method for Three Dimensional Analysis of the Displacement of Spinal Segments", Journal of Bone and Joint Surgery, News Notes, Vol. 55-A, 1973, pp. 435; Brown, R. H., "Instrumental System for Two Plane Radiographic Analysis", Masters Thesis, School of Engineering, Case Western Reserve University, 1972; Brown, R.H. et al. "Spinal Analysis Using a Three-Dimensional Radiographic Technique", Journal of Biomechanics, Vol. 9, 1976, pp. 355–365; Reuben, J. D. et al. "In Vivo Effects of Axial Loading on Healthy Adolescent Spines". Clinical Orthopaedics and Related Research, No. 139, 1979, pp. 17–27.

The system using radio-opaque objects is limited to post-surgical measurements and requires surgery which is often traumatic. In addition the usefulness of this method is limited to the number of markers and the accuracy with which the markers are inserted. In order to improve the system using anatomical landmarks, a modified system has been proposed by De Smet in which three X-ray exposure planes have been used (De Smet et al. "A Radiographic Method for Three-Dimensional Analysis of Spinal Configuration", Radiology, Vol. 137, 1980, pp. 343–348). Eight anatomic landmarks (instead of three or four) have been used in another modified method in order to enhance accurate identification of images (Brown et al. "Clinical Implementation of Bi-plane Radiography: Part I. The System". The Transactions of the 24th Annual Meeting, Orthopaedic Research Society, Vol. 4, 1979, pp. 293).

However, these modifications do not solve the problem of reconstruction of the three-dimensional coordinates of a contour on the object thereby to determine its shape, size, configuration, orientation and position. For a system using anatomical landmarks necessarily suffers from difficulties in the choice of landmarks which can be identified unambiguously in both radiographs.

An object of the present invention is to obviate or mitigate the abovesaid disadvantages.

In one aspect of the present invention there is provided an apparatus for the determination of the three-dimensional coordinates of a contour of an object, the images of the contour being identifiable; the apparatus comprising, radiation means for emitting radiation from at least two spaced locations, film means for exposure to said radiation, the film means being exposed to said radiation means in said at least two locations whereby at least a first and a second two-dimensional image of the said contour are formed on the said film means, said first and second image being located at spaced locations, means for the determination of the spatial coordinates of the radiation means, means for determining two-dimensional coordinates of said first and second two-dimensional images of said contour, processing means for processing said two-dimensional coordinates of said first and second images in which a point is selected on one of said first and second images and is correlated with a point on the other of said first and second images, correspondence means for performing said correlation in which a numerical process is used to find the two-dimensional coordinates of corresponding points on said images which results in an algorithm providing a minimum value, said minimum value defining a corresponding pair of two-dimensional coordinates for a particular three-dimensional coordinate of a point on the contour from which said first and second two-dimensional coordinates of said coordinate pair are produced, whereby corresponding coordinates on said first and second images are identified and processed in pairs, each processed coordinate pair and the spatial coordinates of the radiation means providing the three dimensional coordinate of a point on said identifiable contour.

In another aspect of the present invention there is provided a method of reconstructing the three-dimensional coordinates of a point on an identifiable contour of an object, the method comprising the steps of, irradiating the contour from at least two spaced locations, determining the spatial coordinates of the respective spaced locations, forming a two-dimensional image of the contour for each spaced location, digitizing the coordinates of the two-dimensional images, selecting a first point on one of said contour images, searching on the other of said contour images for a point such that an algorithm provides a minimum value, said minimum value where at the length of a normal tansversal drawn between skew rays which connected the two spaced locations to said two points is at a minimum, defining a corresponding pair of points for a particular point on the contour, processing said corresponding pair with said spatial coordinates of the radiation means to provide said three dimensional coordinates of said point on the contour.

Embodiments of the present invention will now be described by way of example with reference to the accompanying drawings in which:

FIG. 3b is a diagrammatic view of how corresponding point pairs on the 2-dimensional images are obtained in accordance with the flowchart algorithm of FIG. 3a.

FIG. 12 shows the results of a typical in vivo investigation in which the contour of vertebrae L1 (Lumbar 1) is presented in the t-w plane.

Figure 1:
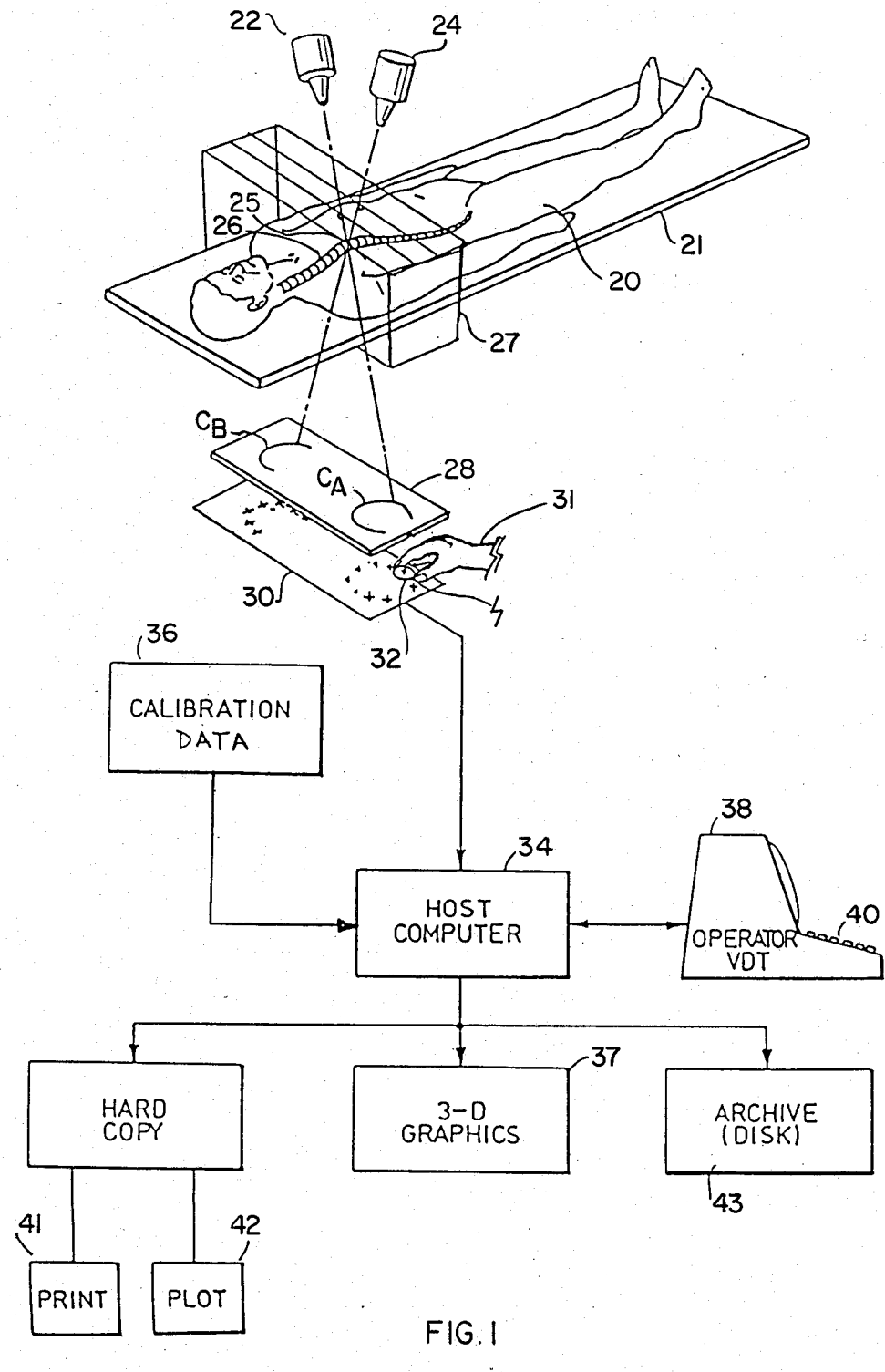
FIG. 1 shows a Contour Radiography system being used on a patient with scoliosis and schematically showing the formation of two 2-dimensional images exposed onto radiographic film.
Figure 3A:
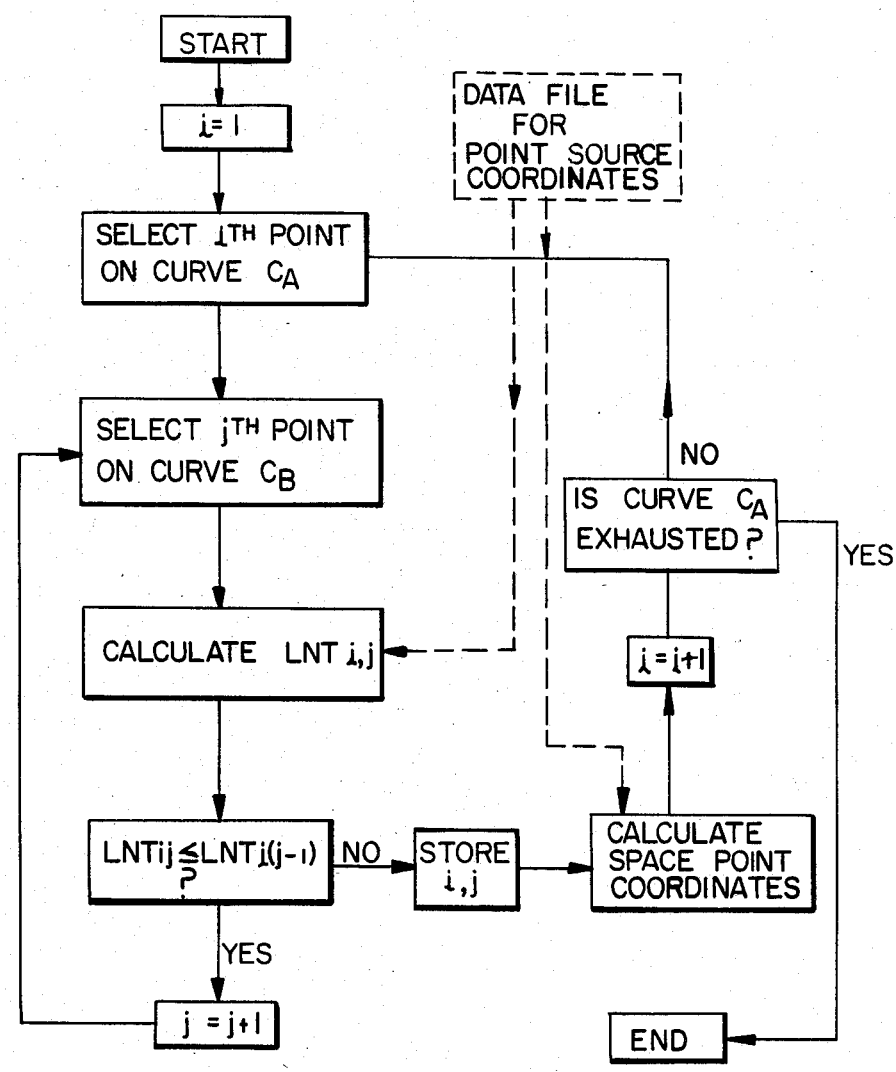
FIG. 3a is a flow chart of the algorithm used to calculate coordinates of points on one image curve which correspond with a point on another image curve for a single point on the contour.

Referring to FIG. 1 a patient 20 with scoliosis is positioned on a table 21 such that two X-ray sources 22 and 24 produce X-rays, some of which intersect in space at the level of a radiographically identifiable contour 25 of a vertebra of the vertebral column 26. A calibration frame 27 is located over the patient 20 to permit spatial determination of X-ray sources $S_1$, $S_2$ as will be described in more detail later. The X-rays produce two distinct image curves $C_A$, $C_B$ of the radiographically identifiable contour 25 on a two-dimensional X-ray film 28 which is located beneath the table 21. The X-ray film 28 is positioned such that image curves $C_A$, $C_B$ are in a common plane. The developed X-ray film is then positioned over a digitizing tablet 30 which may be located at a remote location and an operator 31 uses a digitizing cursor 32 to produce signals representative of the planar coordinates of each point selected (shown by crosses) of the two-dimensional image curves formed on the film by the X-rays. The coordinates of both two-dimensional images are processed in a host computer 34 together with the three-dimensional coordinates of the X-ray sources $S_1$, $S_2$ from calibration data 36, in accordance with the algorithm shown in FIG. 3a to reconstruct the three-dimensional coordinates of points on the radiographically identifiable contour 25. The determined three-dimensional coordinate values are typically processed in a WHIZZARD 7200 graphics display system (Megatek Corporation). The WHIZZARD 7200 graphics system produces an appropriate image on a video display terminal (VDT) 38 which includes a keyboard 40 by which an operator can interact with the graphics display. The VDT image is, of course, displayed in two-dimensions, however all three-dimensions of the reconstructed contour can be seen using an algorithm provided in the WHIZZARD 7200 system such as the WAND 7200 interactive graphics software package, (Megatek Corporation) which causes the two-dimensional image to rotate on the screen of the VDT 38. This permits 360° viewing of the relative orientation and rotation between vertebrae. The image presented on the VDT can be printed or plotted by an associated printer 41 or graph plotter 42 to provide a hard copy and the image can also be archived in a memory such as a disk drive unit 43 for future retrieval and used to compare the orientation and/or rotation of the vertebrae at intervals during different phases of therapy.

Figure 2:
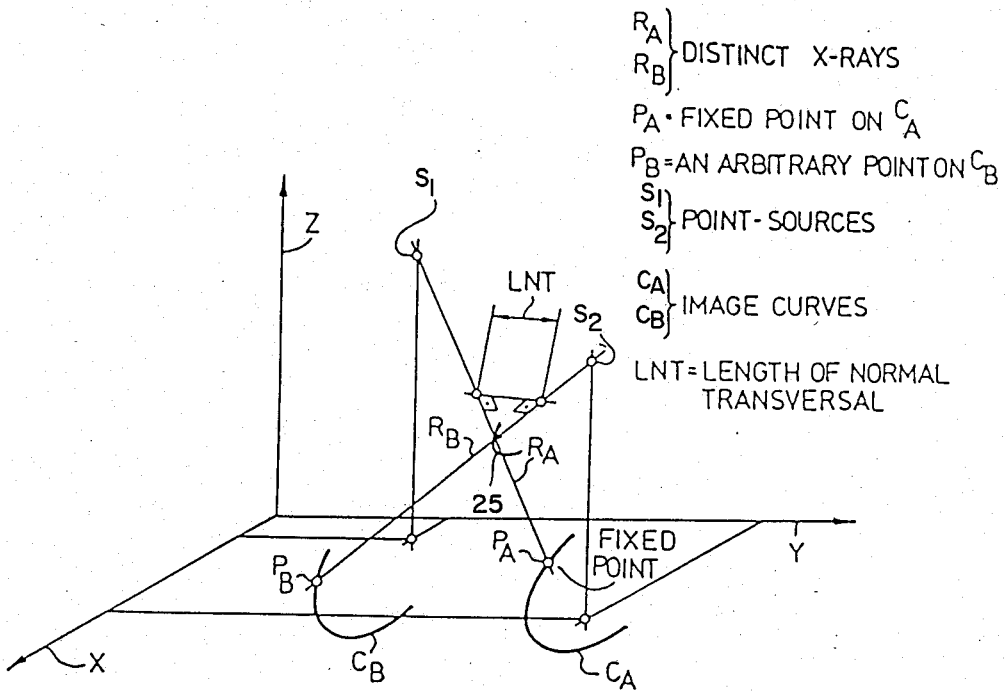
FIG. 2 is a schematic illustration of the theory of Contour Radiography being applied to spatially define the image of a vertebral contour.

The reconstruction of the three-dimensional coordinates of points on the contour of the vertebrae is achieved by a novel technique called Contour Radiography which will now be described in more detail with reference to FIG. 2. X-ray point sources $S_1$ and $S_2$ produce X-rays which produce image curves $C_A$ and $C_B$, respectively, from a radiographically identifiable contour 25 of a vertebra (FIG. 1). The contour 25 is seen, in this embodiment, simultaneously by the two point sources $S_1$ and $S_2$. If we assume that there is a point, $P_A$, on curve $C_A$ which is temporarily fixed it is now necessary to find a point $P_B$ on curve $C_B$ such that the isolated X-rays $R_A$, $R_B$ generated by sources $S_1$ and $S_2$, respectively, will intersect in space. The point of intersection obtained will be the desired target point.

In practice, because of inaccuracies and ever present finite tolerances, it has been found that the possibility of two X-rays exactly intersecting is remote, therefore, what is done with the present technique is to search for two X-rays which are closest to each other. Two non-intersecting X-rays in space form a pair of skew lines and the distance between these skew lines is taken to be the length of their normal transversal, (LNT), i.e. a line which is orthogonal to both skew lines. Therefore, if the LNT of the two lines $R_A$, $R_B$ in space is zero then lines $R_A$, $R_B$ intersect, otherwise they do not. Therefore with this technique a particular X-ray, $R_B$, which provides the minimum LNT value is desired. The practical absolute value of this minimum LNT distance is a few tenths of a millimeter for sufficiently accurate determination of the target point.

Figure 3B:
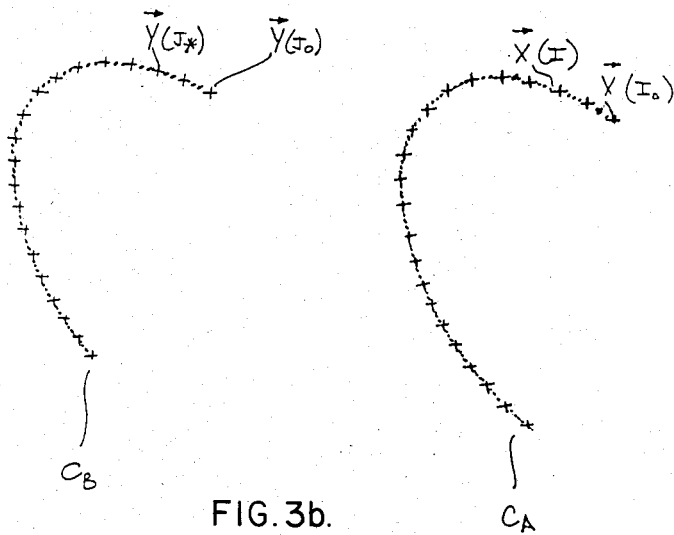
Figure 4:
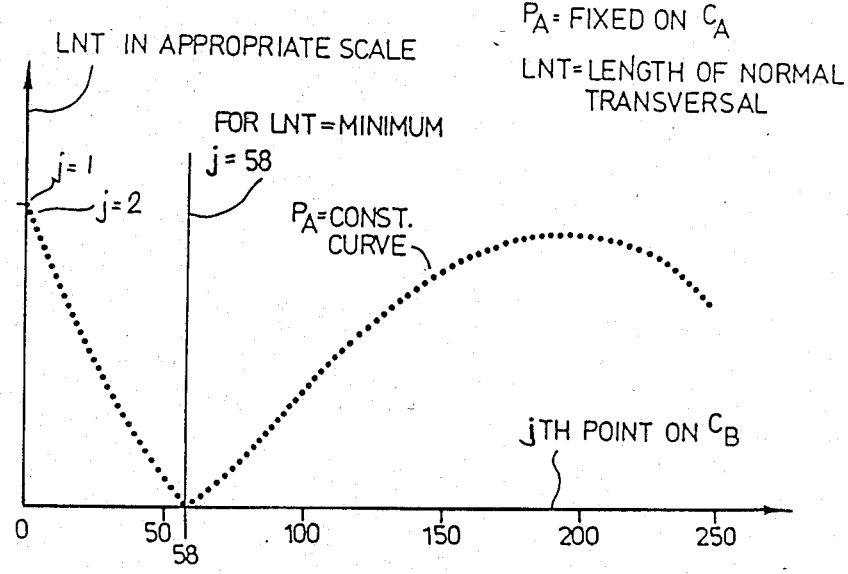
FIG. 4 is a graph of distance between two oriented X-rays in space as curve $C_B$ is traced, point by point, and a particular point on curve $C_A$ is held stationary.

In order to select a single X-ray from the infinite number of X-rays connecting the X-ray source 24 to the curve $C_B$ which would render the LNT minimum, a point, $j=1$, near the end of $C_A$, for example, is selected by the computer 34 and the corresponding LNT is determined as will be described in more detail later. As best shown in FIG. 4, this initial LNT value is usually rather large, and can be several cm. Moving along the curve $C_B$ from the end another point, $j=2$, is selected and the LNT is again determined; generally this LNT will be somewhat shorter than its predecessor. Continuing this process, smaller and smaller LNTs will be obtained, until, finally, the value of LNT starts to increase. If the steps between selected points are sufficiently small, then the $j^{th}$ point tested immediately before the increase of LNT will be at or very near the point for a minimum LNT; in the illustrated case at $j=58$. This is explained with reference to FIG. 3$a$ and with reference to FIG. 3$b$. In FIG. 3$b$ the curves $C_A$ and $C_B$ represent the images of digital coordinates stored in the computer 34. Turning now to FIG. 3$a$, after the operation has started, the computer selects a point ($i=1$) on curve $C_A$ from X and Y values which are stored in the computer memory. For a particular X and Y coordinate value ($i^{th}$) on curve $C_A$, the computer selects an X and Y coordinate value ($j^{th}$) on curve $C_B$. For each selected j value the $LNT_{ij}$ value is computed using the location of the point sources from the calibration image points. The number of i points on curve $C_A$ and j points on curve $C_B$ are usually different since the lengths of the two image curves $C_A$ and $C_B$, which depend on the location of the point sources $S_1$ and $S_2$, are different. Although the number of points initially digitized depends on the selection by the operator, interpolation is also automatically performed between the selected digitized coordinates on each curve in FIG. 8 (shown by crosses) to provide additional points (shown by dots) in order to increase the resolution of the system. The interpolation X and Y values on each curve are used with the calibration data stored in the computer 34 are then used to calculate the length of the normal traversal ($LNT_{ij}$) using a numerical process such that in every case the $i^{th}$ point on curve $C_A$ corresponds to the $j^{th}$ point on curve $C_B$ to generate the numerical relationship $i=f(j)$.

The minimum $LNT_{ij}$ value is then checked to see if it is less than the previous value $LNT_{i,(j-1)}$ and if not, the corresponding point pairs $i^{th}$, $j^{th}$ are stored in the memory of host computer 34. The stored data is then processed by the CONRAD algorithm with the calibration data to the coordinates of the space point on the contour or object-curve and then the algorithm is repeated for the next point $i=i+1$ on curve $C_A$. However, if the point-pair just calculated was based on the last point on the curve (i.e. Curve $C_A$ is exhausted) then the algorithm terminates. In addition, if the LNT is less than the LNT associated with the immediately previous selection of point on $C_B$ then the algorithm automatically jumps to another point on $C_B$ with $j=j+1$. This process is repeated until the inequality $LNT_{ij} < LNT_{i,(j+1)}$ is found false.

As shown in FIG. 4, in this embodiment the $j=58^{th}$ point on $C_B$ tested gives the minimum LNT. Points $j=58^{th}$ (on $C_B$) and i (selected on $C_A$) are then said to correspond. The sought-after target point is now, by definition, taken to be exactly midway on the Normal Transversal (NT) between the two rays $R_A$, $R_B$. A typical LNT value for sufficiently accurate determination of the target point is a few tenths of a millimeter.

Figure 5:
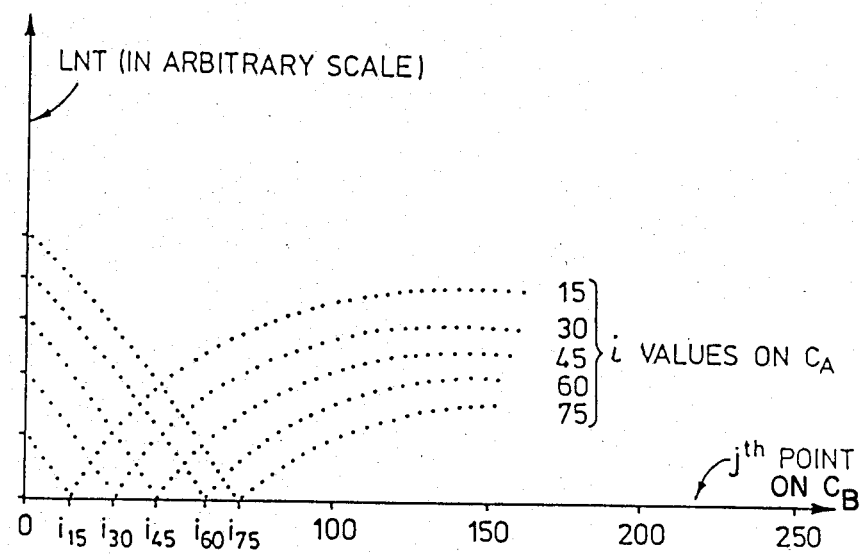
FIG. 5 is similar to FIG. 4 with the exception that here 5 points on the $C_A$ curve are held fixed.

Another point $i=i+1$, on $C_A$, is now selected and the whole algorithm is repeated, yielding another target point. The data continues to be processed by the algorithm, yielding a sufficiently large number of target point locations, by which time the whole target curve or contour of the object body, point-by-point, has been sufficiently determined to permit inspection or examination. FIG. 5 shows a typical case in which five corresponding target points have been identified for different values of i and j. The three-dimensional coordinates of each target point will then be derived from a corresponding point-pair, using the coordinate data of the sources' location.

It will be appreciated that, when the fixed $i^{th}$ point is near one end of curve $C_A$, then the search for its 'corresponding' $j^{th}$ point on $C_B$ should start at the corresponding end of curve $C_B$. Since the images always look similar, this is easy to do. If the search for the corresponding point $C_B$ does not follow this procedure, then the three-dimensional reconstruction algorithm may produce an erroneous space location.

Figure 6:
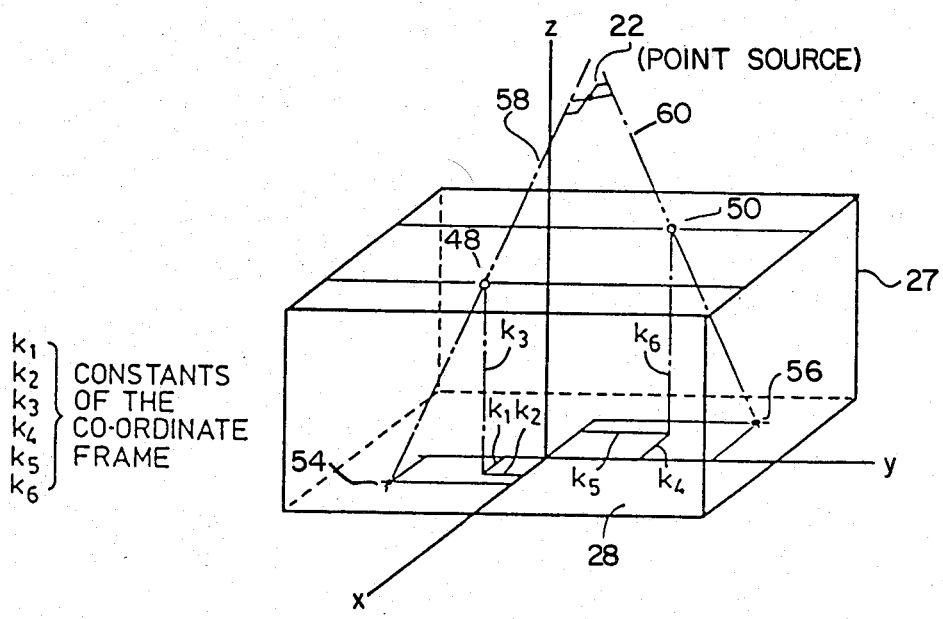
FIG. 6 shows the calibration frame in a Cartesian coordinate geometry system and the principle of the determination of the position of a single point radiation source within this geometry system.

In the above description of FIGS. 2-5 it is assumed that the three-dimensional positions of the two point-sources $S_1$, $S_2$ are known. These assumptions are fulfilled as follows: the coordinate system is a right-handed Cartesian one as shown in FIG. 6; its x and y axes are in the plane of the X-ray film 28 and the z axis points vertically upwards. Since both x and y axes are associated with the image curves, these two axes must also be shown on the X-ray film 28 and then recorded by the digitizing tablet 30. To achieve this the x and y axes are materialized as two X-ray-absorbing very thin steel wires from the coordinate frame 27, the images of which are projected or recorded on the onto the film 28.

The principle of the determination of the two point-sources $S_1$, $S_2$ will best be explained for one point-source $S_1$ although it will be understood that the explanation is also applicable to the second point source. Using an appropriately dimensioned and reasonably rigid coordinate frame 27 as shown in FIGS. 1 and 6, two small lead balls (calibration balls) 48, 50 of approximately 3 mm. diameter are suspended in the frame 27 for calibration purposes. The X-ray film 28 is placed in the frame 27 such that it can occupy only a predetermined position with respect to frame 27. Since the x,y coordinate axes are on the film 28 and the film 28 is immovable with respect to the coordinate frame 27, therefore the x,y axes, on the film, are also immovable with respect to this frame 27. This renders the two suspended calibration balls 48, 50 fixed in the coordinate system, the x, y, z coordinates of the two balls being the constants of the coordinate frame 27 ($k_1, k_2, \ldots k_6$ values in FIG. 6). The positions of the images 54, 56 of the two balls can be read off from the X-ray film 28 and since the positions of the balls themselves are also known, therefore two points on each X-ray generating images of both balls 48, 50 can be determined. Therefore, there are four images of these balls on each X-ray film. Using these two points, the position of the X-rays 58, 60 themselves are then determined. Since both X-rays 58, 60 emanate from the same X-ray point-source 22, therefore, the point source 22, can be located theoretically simply by determining the intersection of these two X-rays. However, by reasons aforementioned in connection with finding the target points, the two X-rays in fact are unlikely to intersect exactly. A search for the most likely position of the X-ray source, is now conducted using the same algorithm as was used to determine the position of a typical target point (explained above); i.e. the sought after target point (in this case the point source 22) will lie, by definition, at the midpoint of the normal transversal between rays 58 and 60.

Figure 7:
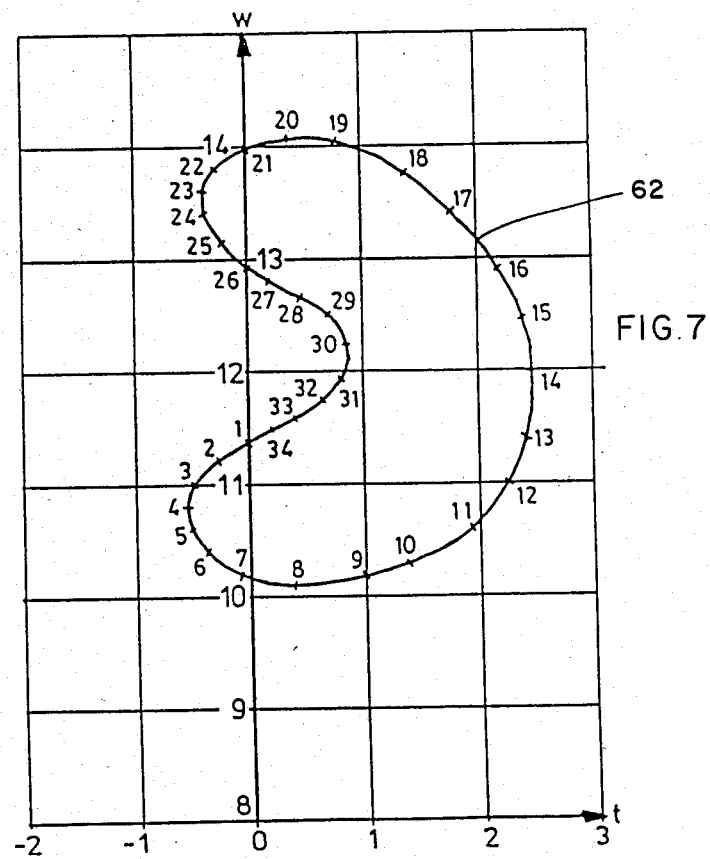
FIG. 7 is an arbitrary original plane curve from which the re-constructed curve is to be produced.

An original test target curve or contour in the display (t, w) system is shown in FIG. 7. Thirty-four points have been used to define the shape of the curve and these locations are indicated on the curve 62. The numbers appearing on the curve are the sequential numbers of points on the curve, starting with 1 and ending at 34.

Figure 8:
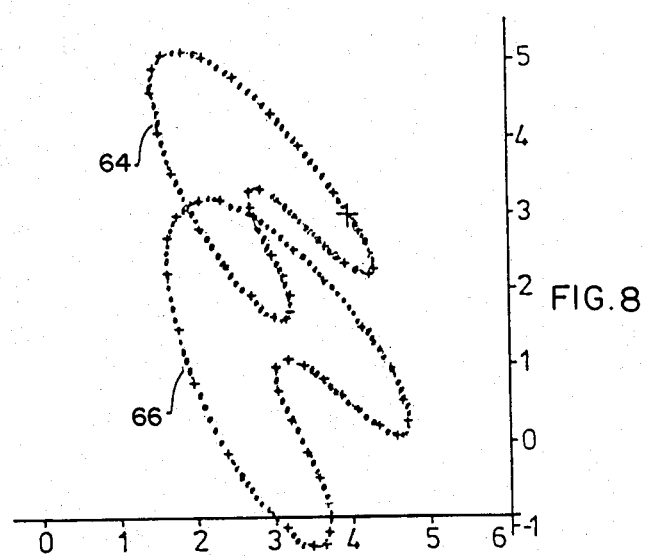
FIG. 8 is a view of two images of the curve of FIG. 7 when projected onto the x-y plane by two point sources.

FIG. 8 shows the typical images 64, 66 of the target curve shown in FIG. 7 as they appear on the x-y coordinate plane of the X-ray film 28. The crosses on curves 64 and 66 correspond to the 34 points on curve 62 of FIG. 3b, and are the selected digitized image points. Curves 62, 64 are of different lengths due to the different spatial location of the X-ray sources.

Figure 9:
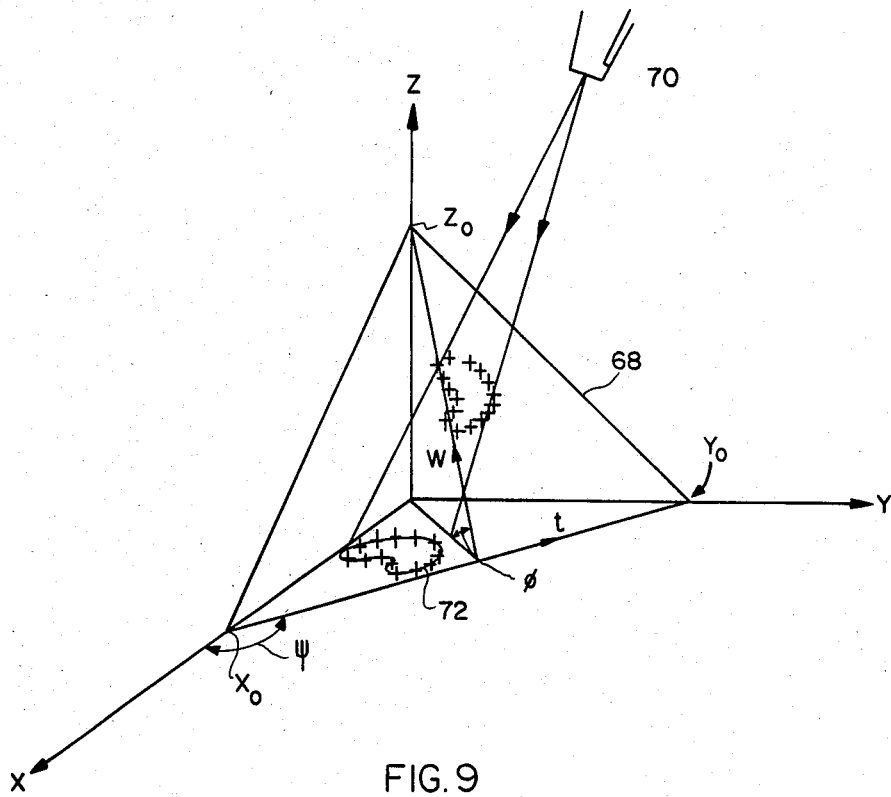
FIG. 9 is a diagram showing the relationship between the t, w coordinate system and the x, y, z coordinate system.

The t, w coordinate system is related to the x, y, z coordinate system as shown in FIG. 9 by the explicit relations of:

$x = f_1(t, w, x_o, y_o$ and $z_o)$
$y = f_2(t, w, x_o, y_o$ and $z_o)$
$z = f_3(t, w, x_o, y_o$ and $z_o)$ Where $f_1, f_2, f_3$ symbolize the functions, t, w the relevant coordinates of a typical target point on the target plane 68 and $x_o, y_o$ and $z_o$ are the x, y, z directional intercepts of the x, y, z axes with the target plane 68.

The angles $\phi$, $\psi$ and intercepts $X_o$, $Y_o$ and $Z_o$ define the position of the t, w plane 68 with respect to the x, y, z coordinate system. The curve in FIG. 7 in the t, w plane is shown projected by a point source 70 to give a curve 72 in the X-Y plane.

Figure 10A:
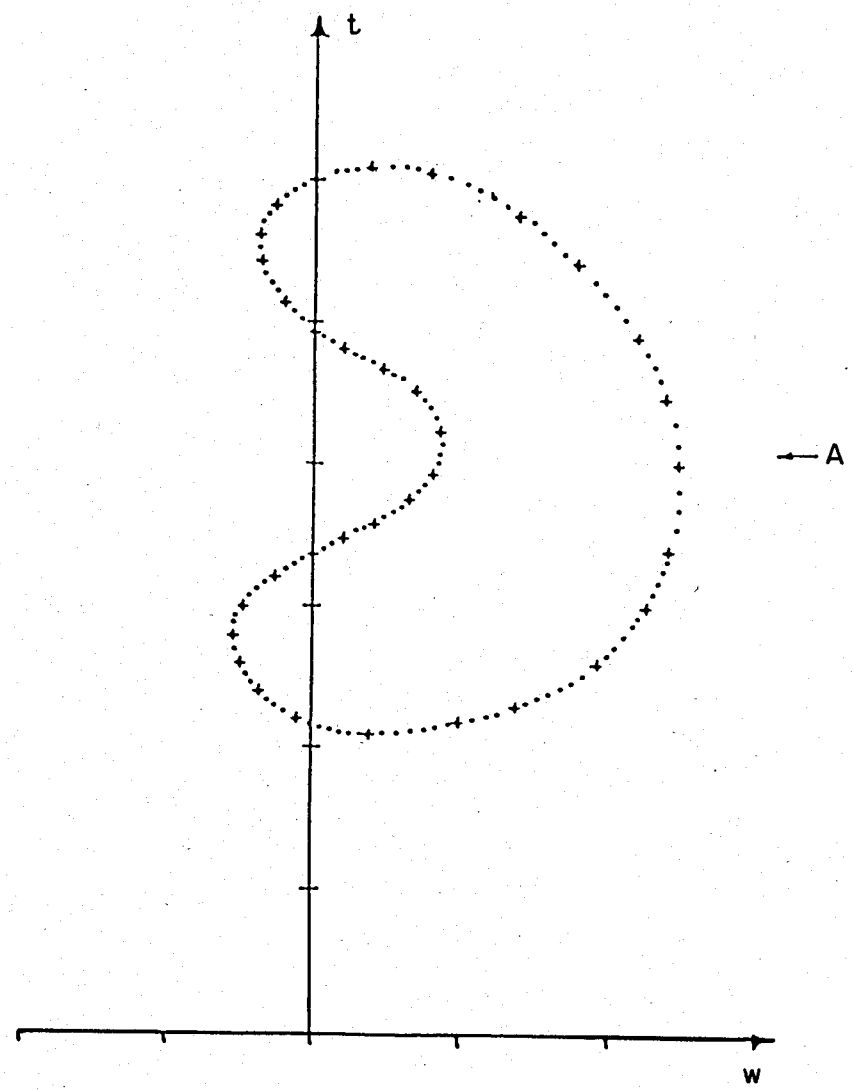
FIG. 10a is a simulation curve in which superimposed original (crosses) and reconstructed (dots) points on the same target curve are shown.
Figure 10B:
FIG. 10b is the curve of FIG. 10a taken in the direction of arrow A.

The curve of FIG. 10a is in orthogonal view; in this view the exact (selected) points (crosses) and the reconstructed points (dots) are superimposed. It is evident from inspection of this figure that the curve formed by the exact points and the curve formed by the reconstructed points are practically indistinguishable. FIG. 10b is another (edgewise) view of the curve of FIG. 10a (taken in direction of arrow A) which demonstrates the effect of superposition in another direction; again it is shows that in this plane the original and the superpositioned points are practically indistinguishable.

Figure 11A:
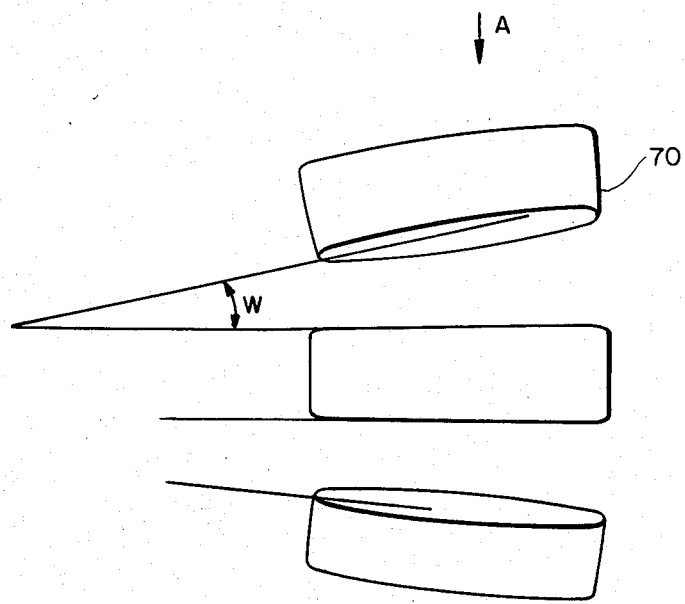
FIGS. 11a and 11b are displays on a Video Display Terminal (VDT) of vertebrae after the three-dimensional coordinates of the points on the contour have been processed by a computer graphics display system.
Figure 11B:
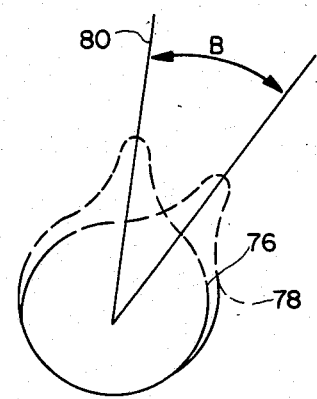

FIGS. 11a and 11b are graphic displays of vertebrae 70 after the three-dimensional coordinates of the points on the contour have been processed by the WHIZZARD 7200 graphics system. The solid lines represent the reconstructed contours and the dotted lines represent lines drawn by the computer to facilitate visual recognition. The angle formed between the planes of adjacent vertebrae, i.e. the "wedge angle $\omega$" is illustrated, and the relative rotation between adjacent vertebrae 76 and 78 with reference to a common axis 80 indicated by angle $\beta$.

By interacting with the VDT 38 using the keyboard 40, an operator, for example a physician, is able to control the orientation of the displays shown in FIGS. 11a and 11b using the WHIZZARD 7200 graphics system 37 to facilitate visualization of the relationship between the vertebrae.

In simulation experiments carried out such as described with reference to FIGS. 7–10b the accuracy of the results is assessed: (a) by visual comparison between the shapes of the reconstructed and exact curves, and, as shown in FIGS. 10a and 10b the two shapes are indistinguishable: and (b) by numerical comparison of the orientations and positions of the reconstructed and exact target planes. In the illustrated (and typical) case the angle between these two planes was found to be 0.023 deg and the average positional error of 5 (similar) cases considered was 0.022 cm in the x and 0.017 cm in the y directions.

In-vivo experiments were performed on 3 scoliotic and 6 non-scoliotic subjects. For each subject the bottom edge of their L1 (Lumbar 1) and top edge of L2 (Lumbar 2) vertebrae were reconstructed. From this data the following relevant characteristics were derived: wedge angle between adjacent vertebrae; orientation of the wedge angle, i.e. position of the intersecting line of the two vertebral planes; absolute and relative position of the vertebrae including relative torsion and lateral shift; size of vertebrae; separation of adjacent vertebrae, i.e. distance between them and the true, i.e. undistorted, shape of the vertebral edge.

A typical case is illustrated in FIG. 12. Here, the t, w coordinate system is in the (reconstructed) target plane—which has a very large inclination of 85.3 degrees (not indicated)—and its t axis is the line connecting the x,y intercepts with the target plane and the w axis contains the z intercept. The M point is the origin of this system and is the foot of the perpendicular dropped from the origin of the x,y system to the intersecting line of the target and x,y planes.

From the figure it can be seen that the size of vertebrae is about 3.2×2.5 cm, its symmetry axis is inclined to the vertical plane to about 19 degrees and its center-point is situated at about w=14.75 cm above the x-y plane (X-ray film).

It was found that the average wedge angle between adjacent vertebrae of a scoliotic spine is larger than that of a non-scoliotic one—an expected finding if one considers that the scoliosis imposes wedging in the frontal plane which is superimposed on the (normal) kyphotic angulation which takes place in the sagittal plane. The two angles added vectorially produces a larger absolute angle than the kyphotic spine (alone) does.

In the case shown in FIG. 12 the following characteristics were determined in-vivo: inclination of vertebral planes to horizontal: 85.3 degrees for L1—bottom; 78.0 degrees for L2—top; wedge angle between adjacent vertebrae=8.9 degrees; turn of L1 in its own plane away from vertical=19 degrees; inclination of the intersecting line of the two vertebral planes to the horizontal=34.9 degrees; size of L1=2×3.5 cm.; position of centerpoint of L1 is x= −9.45 cm, y=1.71 cm, z=14.7 cm and the distance between L1—bottom and L2—top=0.71 cm.

The estimated inaccuracies for these determinations were approximately 2 degree angular and 0.2 cm linear.

It should be understood that various modifications may be made to the embodiment described without departing from the scope of the invention. Thus, a single X-ray source could be used and moved between two positions in order to create two images of the radiographically identifiable contour. The algorithm for reconstruction of the three-dimensional coordinates would operate in the same way with the contours produced on the X-ray film with the source in different positions. In addition, the graphics system need not be a WHIZZARD 7200 system but any system which provides three-dimensional simulation such as rotation and translation effects on a screen. The graphics system could also be conveniently housed in the same unit as the host computer. Furthermore, in this technique it should be understood that, there is no requirement for the object curve contour to be on any particular plane, and it does not even have to be a planar curve, indeed, it may be a space-curve of any configuration, e.g., spiral. The object curve need not be continuous along its entire length, although the reliability of the obtained results increases with the increased length of its continuous part. The contour can be absolutely smooth that is, devoid of any distinguishing feature which can be identified on the images such as 'landmarks' or 'hardpoints'. The X-ray sources could also be positioned using commercially available three-dimensional displacement transducers. Also, the determination of position of a typical X-ray point source may be made by some other means than that is illustrated in FIG. 6.

It should also be appreciated that the invention can also be used with any object which has an identifiable contour which can be irradiated from two spaced locations by a source of radiation not necessarily X-rays, for example light or ultrasound, to form at least two separate two-dimensional images corresponding to the respective locations of the electromagnetic radiation source, the two-dimensional images being spaced apart. The invention is not therefore limited to use with X-ray sources for visualizing internal contours of the human or animal body or for inspecting the contents of an opaque walled container. The invention could be used for example in reconstructing the three-dimensional coordinates of a road or any other identifiable contour from aerial photographs.

Following the simulation experiments, it was concluded that in order to enhance accuracy the target curve or contour should be closer to the image plane, rather than to the source; the horizontal separation of the point-sources should be large; if the target is oblong (elliptical) then the line connecting the two point-sources should be parallel to the major axis of the ellipse rather than perpendicular to it; the foot of the target point should fall between its two images, and, generally, edgewise views of the target should be avoided. The algorithm for reconstruction of the three-dimensional coordinates result in inaccuracies in the situation where the image point is at a common point of tangency, i.e. points of the two images which have the same tangent, when this occurs it is difficult to determine the target location in proximity to these points. This restriction is not a major impediment since only a few percent of the total available points is affected.

Advantages of the embodiment are that the tracing of the spatial object is automatic and is accomplished by the Contour Radiography (CONRAD) algorithm, and the method follows the configuration of even a complex space curve; no 'a-priori' knowledge of the position of the target contour is necessary; most importantly Contour Radiography does not rely on the existence of any anatomical landmarks or implanted hardpoints; consequently, the image curves are allowed to be smooth and completely featureless; an almost-continuous description of the object-curve is possible; the resolution of the reconstructed shape is limited only by the resolution (sharpness) of images on X-ray film; the use of Contour Radiography is not conditional upon the stereoscopic vision of the operator; Contour Radiography is relatively fast; with a hardwired computer the whole process takes 3–4 minutes and the patient is held immobile for only a few seconds; the accuracy of the results is mainly limited only by the digital process employed. All in all, Contour Radiography has been demonstrated to be suitable for determination of positional and configurational properties of an internal anatomical body (e.g. vertebra).

We claim:

1. Apparatus for the determination of the three-dimensional coordinates of a contour of an object, the images of the contour being identifiable, the apparatus comprising:

radiation means for emitting radiation from at least two spaced locations;

film means for exposure to said radiation, the film means being exposed to said radiation means in said at least two spaced locations whereby at least a first and a second two-dimensional image of the contour are formed on the film means at spaced locations;

calibration means for determining the spatial coordinates of the radiation means;

means for determining the two-dimensional coordinates of said first and second two-dimensional images of the contour;

processing means for processing said two-dimensional coordinates of said first and second images in which a point is selected on one of said first and second images and is correlated with a point on the other of said first and second images;

correspondence means for performing said correlation in which an algorithm is used to determine a minimum value for the length of the normal transversal drawn between skew rays of radiation from said two spaced locations, which skew rays connect the two spaced locations to respective points on said first and second images, said minimum value thereby defining a corresponding pair of two-dimensional coordinates for each three-dimensional coordinate, which three-dimensional coordinate represents a point on the identifiable contour of the object, whereby corresponding coordinates on said first and second images are identified and processed in pairs, each processed coordinate pair and the spatial coordinates of the radiation means providing the three-dimensional coordinates of a point on the identifiable contour.

2. Apparatus as claimed in claim 1 wherein a first and a second radiation means is provided, said first and second radiation means providing respective first and second two-dimensional images on said film means.

3. Apparatus as claimed in claim 2 wherein the calibration means is a frame located between the first and second radiation means and the film means.

4. Apparatus as claimed in claim 2 wherein the calibration means is associated with first and said second radiation means, said calibrations means being a three-dimensional displacement transducer means.

5. A system as claimed in claim 1 wherein said radiation means is movable between first and second locations, to provide respective first and second two-dimensional contour images.

6. Apparatus as claimed in claim 5 wherein the radiation means is an X-ray source and the calibration means is a calibration frame located between the X-ray source and the film.

7. Apparatus as claimed in claim 6 wherein the calibration means is a three-dimensional displacement transducer means associated with the radiation means.

8. Apparatus for reconstruction of three-dimensional coordinates of an object, which object has a radiographically identifiable contour, the apparatus comprising:
an X-ray source for emitting X-rays, said source being movable between a first and a second position;
X-ray film for exposure to said X-rays;
the object being located between the X-ray source and the X-ray film;
calibration means located between the X-ray source and the X-ray film for calibrating the spatial location of the X-ray source; whereby the X-ray film is exposed in said first and second positions so as to obtain respective first and second two-dimensional contour images of the radiographically identifiable contour on said X-ray film at spaced locations, and whereby calibrations images of the X-ray source are obtained on said X-ray film;
means for providing two-dimensional coordinates of said first and second contour images and of said images of said calibration means;
processing means for processing the two-dimensional coordinates of said first and second images in which a two-dimensional coordinate selected on one of said first and second images is correlated with a two-dimensional coordinate on the other of said first and second images;
correspondence means for performing said correlation in which an algorithm is used to determine a minimum value for the length of the normal transversal drawn between skew rays which connect the X-ray source in said first and second positions to respective points on the first and second contour images, said minimum value thereby defining a corresponding pair of two-dimensional coordinates for each three-dimensional coordinate, which three-dimensional coordinate represents a point on the identifiable contour of the object, whereby corresponding coordinates on said first and second images are identified and processed in pairs, each processed coordinate pair and the spatial coordinates of the X-ray source providing the three-dimensional coordinate of a point on the identifiable contour.

9. Apparatus as claimed in claim 8 wherein said reconstructed three-dimensional coordinates of said radiographically identifiable contour are processed in a three-dimensional graphics display system, said system including a visual display unit, said system reconstructing an image from said three-dimensional coordinates of said radiographically identifiable contour, and displaying this image on said visual display unit.

10. Apparatus for reconstruction of three-dimensional coordinates of an object which has a radiographically identifiable contour, the apparatus comprising:
a first and a second X-ray source for emitting X-rays;
an X-ray film for exposure to said X-rays, the object with the radiographically identifiable contour being located between the X-ray source and the X-ray film;
calibration means located between the X-ray source and the X-ray film to determine the locations of the first and second X-ray sources;
said X-ray film being exposed to the first and second X-ray sources whereby respective first and second two-dimensional contour images of said radiographically identifiable contour are obtained on said X-ray film at spaced locations, and whereby calibration images of said calibration means are obtained on said X-ray film;
means for providing two-dimensional coordinates of said first and second contour images and of said calibration images;
processing means for processing the two-dimensional coordinates of said first and second images in which a two-dimensional coordinate selected on one of said first and second images is correlated with a two-dimensional coordinate on the other of said first and second images;
correspondence means for performing said correlation in which an algorithm is used to determine a minimum value for the length of the normal transversal drawn between skew rays which connect the first and the second X-ray sources to respective points on said first and second contour images, said minimum value thereby defining a corresponding pair of two-dimensional coordinates for each three-dimensional coordinates of a point on the identifiable contour of the object, whereby corresponding coordinates on said first and second images are identified and processed in pairs, each process coordinate pair and the spatial coordinates of the first and second X-ray sources providing the three-dimensional coordinate of a point on said identifiable contour.

11. Apparatus as claimed in claim 10 wherein said X-ray film is exposed simultaneously to said first and second X-ray sources.

12. Apparatus as claimed in claim 11 wherein said reconstructed three-dimensional coordinates of said radiographically identifiable contour are processed in a three-dimensional graphics display system, said system including a visual display unit, said system reconstructing an image from said three-dimensional coordinates of said radiographically identifiable contour, and displaying this image on said visual display unit.

13. A method of reconstructing the three-dimensional coordinates of a point on an identifiable contour of an object, the method comprising the steps of:
irradiating the contour from at least two spaced locations;
determining the spatial coordinates of the respective spaced locations;

forming a two-dimensional image of the contour for each spaced location;

digitizing the coordinates of the two-dimensional images;

selecting a first point on one of said contour images;

searching on the other of said contour images for a point such that an algorithm provides a minimum value whereat the length of a normal transversal drawn between skew rays which connect the two spaced locations to said point is at a minimum, said minimum value defining a corresponding pair of points for a particular point on the contour;

processing said corresponding pair with said spatial coordinates of the radiation means to provide said three-dimensional coordinates of said point on the contour.

14. A method as claimed in claim 13 wherein said contour is simultaneously irradiated with radiation from said at least two spaced locations.

15. A method as claimed in claim 13 or 14 including repeating said selection for a plurality of points on the contour and providing a sufficient number of corresponding point pairs to identify said contour in space.

16. A method as claimed in claim 15 including the step of processing the three-dimensional coordinates with a three-dimensional graphics display system to provide a visual display of said contour.

* * * * *